(12) United States Patent
Pasquet et al.

(10) Patent No.: US 11,160,584 B2
(45) Date of Patent: Nov. 2, 2021

(54) DEVICE FOR ATTACHING A FLAT BAND ON A BONE PART

(71) Applicant: IMPLANET, Martillac (FR)

(72) Inventors: Denis Pasquet, Aix-en-Provence (FR); Régis Le Couëdic, Bordeaux (FR)

(73) Assignee: IMPLANET, Martillac (FR)

( * ) Notice: Subject to any disclaimer, the term of this patent is extended or adjusted under 35 U.S.C. 154(b) by 127 days.

(21) Appl. No.: 16/564,368

(22) Filed: Sep. 9, 2019

(65) Prior Publication Data

US 2020/0000496 A1 Jan. 2, 2020

Related U.S. Application Data

(62) Division of application No. 15/544,352, filed as application No. PCT/FR2016/050096 on Jan. 19, 2016, now Pat. No. 10,433,879.

(30) Foreign Application Priority Data

Jan. 20, 2015 (FR) ...................................... 1550441

(51) Int. Cl.
| | | |
|---|---|---|
| A61B 17/70 | (2006.01) | |
| A61B 90/00 | (2016.01) | |
| A61B 17/82 | (2006.01) | |
| A61B 17/84 | (2006.01) | |
| A61B 17/56 | (2006.01) | |

(52) U.S. Cl.
CPC .......... *A61B 17/7053* (2013.01); *A61B 17/82* (2013.01); *A61B 17/842* (2013.01);
(Continued)

(58) Field of Classification Search
CPC ............ A61B 17/0401; A61B 17/0487; A61B 17/7053; A61B 17/82; A61B 17/842;
(Continued)

(56) References Cited

U.S. PATENT DOCUMENTS

| 4,455,717 A | 6/1984 | Gray |
|---|---|---|
| 5,356,412 A | 10/1994 | Golds et al. |

(Continued)

FOREIGN PATENT DOCUMENTS

EP    2316363 A1    5/2011

OTHER PUBLICATIONS

International Search Report dated Apr. 13, 2016, issued in corresponding International Application No. PCT/FR2016/050096, filed Jan. 19, 2016, 7 pages.

(Continued)

*Primary Examiner* — Pedro Philogene
(74) *Attorney, Agent, or Firm* — Christensen O'Connor Johnson Kindness PLLC (57) ABSTRACT

A method for attaching a flat and flexible band on at least one bone part is disclosed. The band includes two end portions. A rigid base body crossed by an opening, and a retaining part that can be inserted in the opening is employed. The retaining part is at least partially in the shape of a squeezable wedge comprising a central bore for passage of the end portions facing the flexible band, the bore having a transverse cross-section that can be deformed between a first cross-section for free passage of the end portions when the part has not been inserted in the opening and a second cross-section for locking the end portions by compression when the part is entirely or substantially entirely inserted in the opening.

8 Claims, 4 Drawing Sheets

(52) U.S. Cl.
CPC ............ *A61B 90/03* (2016.02); *A61B 17/707* (2013.01); *A61B 17/7067* (2013.01); *A61B 2017/564* (2013.01); *A61B 2090/034* (2016.02)

(58) Field of Classification Search
CPC .............. A61B 17/7067; A61B 17/707; A61B 2017/0445; A61B 2017/0403; A61B 2017/0458; A61B 2017/0409; A61B 2017/0451; A61B 2017/0488; A61B 2017/045; A61B 2017/564; A61B 90/03; A61B 2090/034
See application file for complete search history.

(56) References Cited

U.S. PATENT DOCUMENTS

| | | | | |
|---|---|---|---|---|
| 5,383,905 | A * | 1/1995 | Golds | ................ A61B 17/0487 24/136 L |
| 5,609,634 | A * | 3/1997 | Voydeville | ......... A61B 17/7062 606/248 |
| 6,582,433 | B2 * | 6/2003 | Yun | .................... A61B 17/7062 606/249 |
| 6,589,246 | B1 | 7/2003 | Hack et al. | |
| 7,879,072 | B2 | 2/2011 | Bonutti et al. | |
| 9,345,518 | B2 * | 5/2016 | Larroque-Lahitette | ...................... A61B 17/7053 |
| 10,010,359 | B2 | 7/2018 | Garcia et al. | |
| 10,314,623 | B2 * | 6/2019 | Alamin | .............. A61B 17/7055 |
| 2015/0032154 | A1 | 1/2015 | Kaplan | |

OTHER PUBLICATIONS

Written Opinion of the International Searching Authority dated Apr. 13, 2016, issued in corresponding International Application No. PCT/FR2016/050096, filed Jan. 19, 2016, 6 pages.

International Preliminary Report of Patentability dated Jul. 25, 2017, issued in corresponding International Application No. PCT/FR2016/050096, filed Jan. 19, 2016, 1 page.

* cited by examiner

DEVICE FOR ATTACHING A FLAT BAND ON A BONE PART

CROSS-REFERENCES TO RELATED APPLICATIONS

This application is a division of U.S. patent application Ser. No. 15/544,352, filed Jul. 18, 2017, which is the National Stage of International Application No. PCT/FR2016/050096, filed Jan. 19, 2016, which claims the benefit of French Application No. 1550441, filed Jan. 20, 2015, all the disclosures of which are incorporated by reference herein.

TECHNICAL FIELD

Embodiments of the present disclosure relate to a device for attaching a flat and flexible band on at least one bone part.

They also relate to a method for attaching a flat and flexible band using such a device.

It has a particularly important but not exclusive application in the consolidation of the vertebral column and, in particular, in the union of two vertebrae in cases of damage.

BACKGROUND

It is known that the intervertebral discs may be subject to compression, herniation, or arthritic intervertebral degeneration.

To manage the patients, there are techniques that require a surgical intervention.

A first technique involves replacement of the damaged disc with an intervertebral disc prosthesis. Such a replacement procedure is difficult for the surgeon to perform and poses a risk of loosening under the effect of the considerable shearing forces that arise in particular when the prosthesis is in the position of maximum flexion.

A second technique involves performing intervertebral arthrodesis, an operation by which the two vertebrae adjacent to the damaged disc can be fused. This blocks the degeneration of the disc, on account of the suppression of any mobility between the two vertebrae concerned.

Such a technique entails the use of a device for stabilizing the two vertebrae, device generally having screws which are intended to be screwed into the vertebrae and connected to each other by a rigid connection member. It is thus possible to avoid excessive mechanical stresses being applied to the intervertebral disc.

Here again, there are disadvantages in particular in requiring screwing into the vertebrae, which is a structurally aggressive operation that weakens the vertebrae concerned, or which is in fact impossible if the vertebrae are in a poor condition and/or are insufficiently wide at the attachment region.

Another technique involves the use of hooks. This approach, however, is a very delicate one, since the operating surgeon must not touch the spinal cord, in order to avoid paralyzing the patient. These are also risks of the hooks slipping and/or of the hooks coming loose.

SUMMARY

Embodiments of the present disclosure aim to make available a device which serves for attachment on a bone part and which is better than the previously known devices in terms of meeting the demands that arise in practice, especially as it is not limited to attaching at least two bone parts to each other, it permits greater flexibility, it avoids any intrusion into the bone, and it poses no risk of slipping and/or of losing tension on the vertebrae, all this at a low cost and/or at less cost than with the devices of the prior art.

It also has the advantage of permitting easy handling of the flexible band, allowing the latter to be easily placed around the bone parts by the surgeon.

To this end, the disclosure proposes in particular a device for attaching a flat and flexible band on at least one bone part, comprising the band having two end portions, a rigid base body with a through-opening, and a retaining component that is insertable in the opening, characterized in that the retaining component is at least partially in the shape of a squeezable wedge comprising a central bore for passage of the opposite end portions of the flexible band, the bore having a cross section that is deformable between a first cross section for free passage of the end portions when the component has not been inserted in the opening, and a second cross section for blocking the end portions by compression when the component is entirely or substantially entirely inserted in the opening.

In advantageous embodiments, use is also made of one or more of the following arrangements:

With the base body extending about an axis, the opening has a first longitudinal cross section that is an isosceles trapezoid or substantially an isosceles trapezoid in a first axial plane with a first angle at the base a, and the retaining component has a second longitudinal cross section that is an isosceles trapezoid or substantially an isosceles trapezoid in the first axial plane with a second angle at the base b>a.

Substantially trapezoidal means a cross section of geometric shape in which the sides of the trapezoid have a periphery inscribed within a trapezoid but are not necessarily linear or formed by a straight line (by being toothed, for example).

The retaining component comprises two opposite longitudinal end walls, each of the longitudinal end walls being provided with a continuous slit which is arranged on a portion of the wall, is open to the bore and opens out on the upper face of the component.

The slits or cuttings promote the squeezing of the component during its introduction with force into the opening, while at the same time permitting from the outset a bore that is as wide as possible, which makes it easier for the ends of the band to be introduced and passed through before compression.

The inner face of the opening and the outer peripheral face of the component comprise means for pre-connection to each other by snap-fit action.

These means for pre-connection have a role as non-return means permitting preliminary assembly of the device, for example to avoid the various elements of the device coming apart in a transporting package and then having to be looked for and put together by the surgeon at the time of the intervention.

The inner face of the opening of the body and the outer peripheral face of the component have means constituting a system for blocking the component with respect to the body when the component is inserted in the opening.

The bore and the component each have a longitudinal plane of symmetry, respectively defining two opposite inner longitudinal faces for the opening and two opposite outer peripheral longitudinal faces for the component, each opposite face having at least one portion provided with at least one tooth or rib for fastening and blocking the component with respect to the body when the component is inserted in the opening.

These fastening means permit preliminary positioning in the alignment of the elements with respect to each other, which will allow them to be compressed easily by ancillary gripping forceps of a design known to a person skilled in the art.

They likewise constitute a non-return system that prevents disassembly of the component and of the body when the component is inserted in the body.

The outer peripheral longitudinal faces of the component are at least partly inclined with respect to the plane of symmetry in order to give the wedge shape.

The bore has a cross section of oblong shape and has two opposite main walls, at least one main wall comprising, on its inner face, at least one inwardly protruding transverse rib. Advantageously, it comprises two opposite ribs which are offset in height.

The protruding transverse rib is situated in the upper longitudinal part of the bore.

The bore and the retaining component are of shapes that are designed to cooperate by friction on at least one of their opposite parts in the direction perpendicular to the first longitudinal plane when the component is inserted in the opening.

The component has a core hollowed out by the bore, of general oblong shape, comprising two opposite inclined main walls forming the wedge and two end walls extending about an axis, of which the faces are arranged to cooperate longitudinally with a corresponding recessed part of the opening, the thickness of the junctions between main walls and end walls being reduced and designed to permit the deformation by squeezing in the transverse direction without deformation in the longitudinal direction during insertion of the component in the opening.

Such an arrangement allows the component to deform in one plane, in the desired direction of wedging, while maintaining an excellent guiding capacity without deformation/expansion in the other plane perpendicular to the first one.

Advantageously, the end walls extending about an axis are each provided with at least one transverse slit along part of its height to promote squeezing.

The base body is made of titanium, the retaining component is made of polymer, and the flexible band is a polymer braid.

The disclosure also relates to a method for attaching a flat and flexible band on at least one bone part, comprising the band provided with two end portions, a rigid base body with a through-opening, and a retaining component that can be inserted into the opening, characterized in that, with the retaining component being in the shape of a squeezable wedge comprising a central bore for passage of the opposite end portions of the flexible band, an end portion of the band is introduced into the opening and into the bore, the component being connected partially (beforehand or subsequently) in the opening, the band is passed around the bone part, the other end portion is passed through the opening and the bore, thus forming a loop for gripping the bone part, the loop is tightened to the desired size by pulling on the two end portions, and the component is inserted with force into the opening, deforming the bore in order to obtain a position in which the end portions are blocked by compression in the bore, the component then being deformed plastically.

Advantageously, at least two adjacent vertebrae are joined together in the case of an arthrodesis procedure.

To do this, an end portion of the band is passed through the base body and the component, the flat band is placed around the two vertebrae (or forms a loop with the rest of the band around the vertebrae), and the other end portion is passed through the opening and the bore, the vertebrae are brought closer by pulling on the ends, and the attachment is blocked by inserting the component with force into the body in the desired position, before cutting off the excess end positions of the band.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

DETAILED DESCRIPTION

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

Figures 1A, 1B:
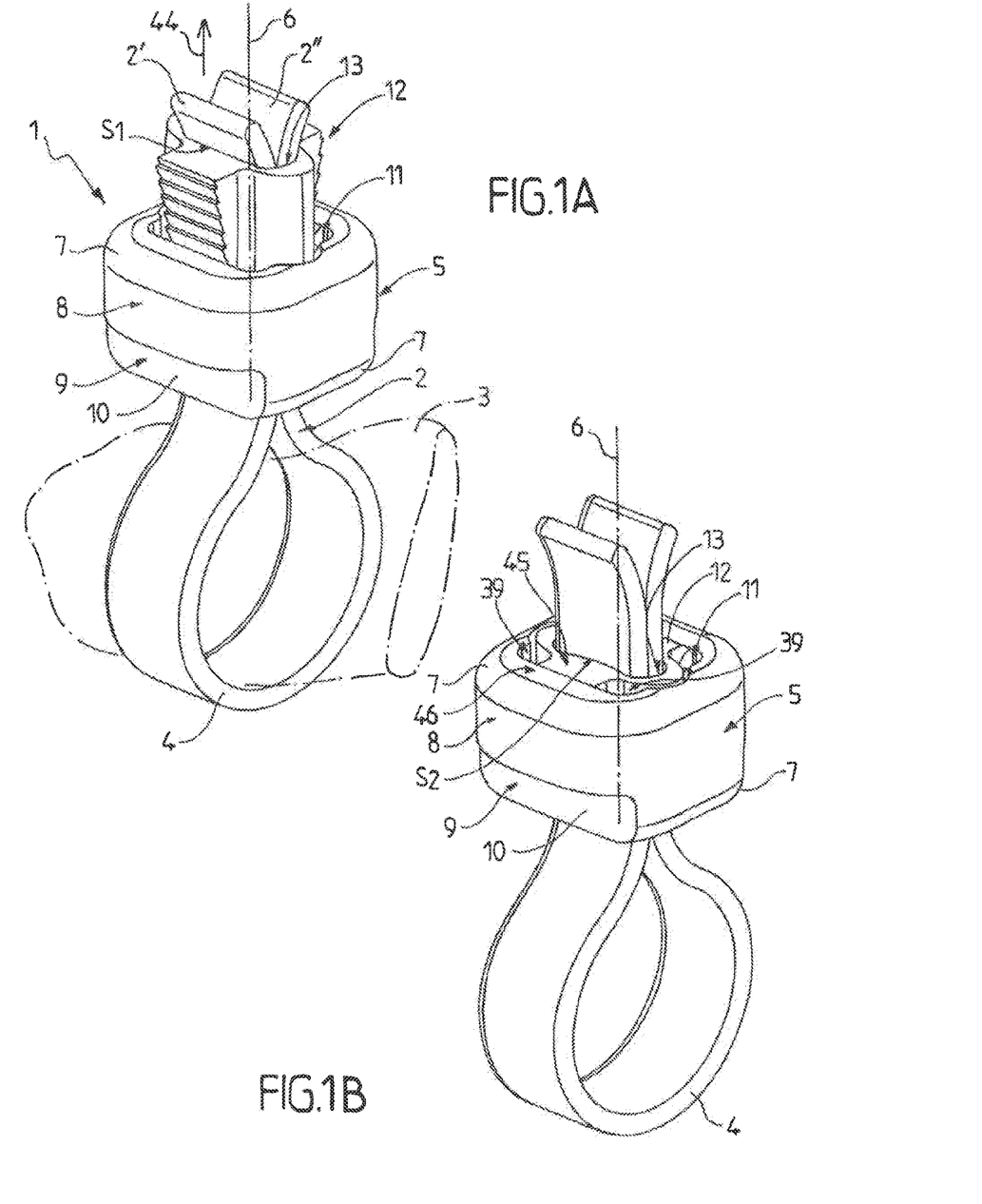
FIGS. 1A and 1B are perspective views of a device according to an embodiment of the disclosure, before insertion (FIG. 1A) and after complete insertion (FIG. 1B) of the retaining component into the base body.

FIGS. 1A and 1B show a device 1 for attaching a flat and flexible band 2 on at least one bone part 3. The band 2 is, for example, made of braided polyester, for example polyester with a thickness of 1 to 3 mm and a width of 6 mm, and has a loop 4 for attachment on the bone part 3, for example on a transverse or spinous process of a vertebra. The loop 4 is formed by bringing together the two end portions 2' and 2" of the band.

The device 1 also comprises a rigid base body 5, for example made of titanium, although it can also be made of rigid plastic material. The body 5 extends about an axis 6. It is of a substantially parallelepipedal or cuboid shape with edges 7 which, for example, are rounded, for example with a widened upper part 8 and a transversely narrowed lower part 9 in order to form two lateral recesses 10 that will allow it to be gripped by the jaws of ancillary forceps.

It is provided with a through-opening 11 which has a substantially oblong cross section and which will be explained in detail with reference to FIGS. 4 to 4B.

The device 1 moreover comprises a component 12 which serves to retain the band 2 and which is made of plastic material, for example, and is at least partially wedge-shaped, that is to say with a prismatic or substantially prismatic shape, as will be explained in detail with reference to FIGS. 2 and 2A to 2C.

The component 12 has a bore 13 running through it for the passage of the ends 2', 2" of the band, the bore 13 having a cross section that is deformable between a first cross section $S_1$ for the free passage of the end portions when the component 12 is not inserted with real compression in the opening (FIG. 1A), and a narrowed cross section $S_2$ for blocking the end portions by compression when the component is inserted fully in the opening 11 (FIG. 1B).

Figures 2, 2A, 2C:
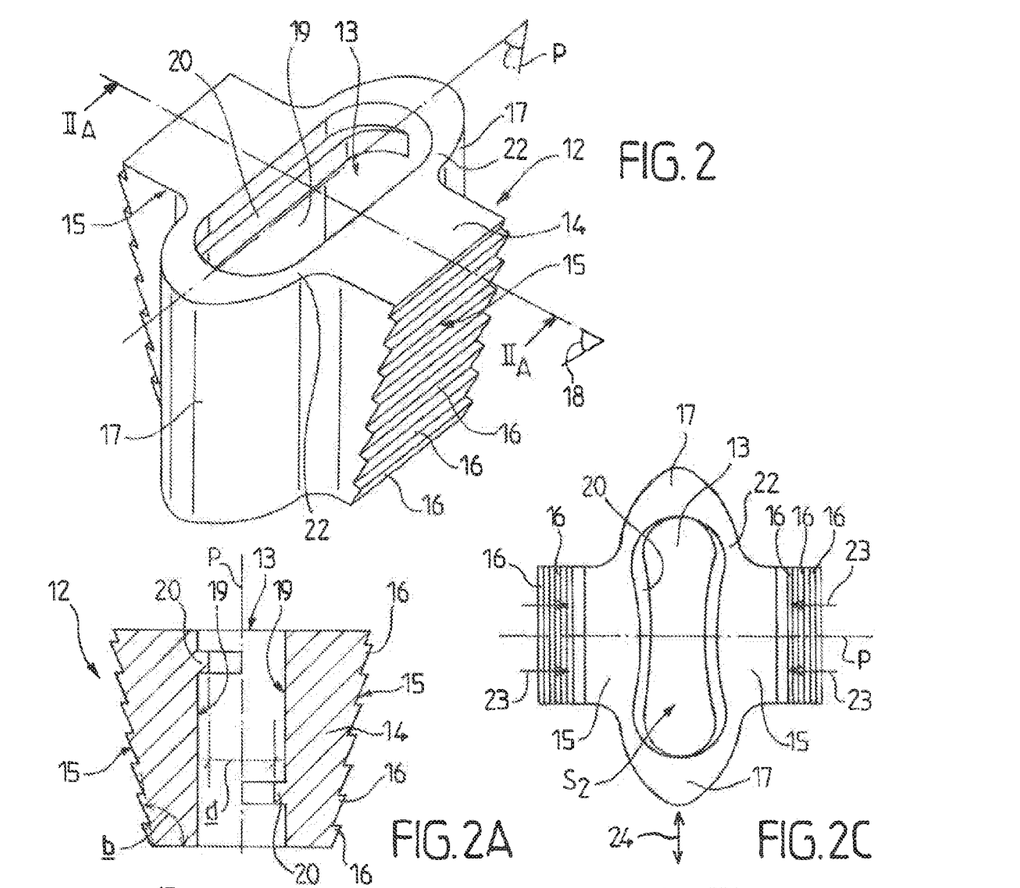
FIG. 2 is a perspective view of the retaining component from FIG. 1.
FIGS. 2A, 2B and 2C are, respectively, the cross section IIA-IIA from FIG. 2 (FIG. 2A), the plan view before insertion (FIG. 2B) and after insertion (FIG. 2C) of the component from FIG. 2.

With reference to FIG. 2, the component 12 has a first central part 14 with a horizontal cross section that is rectangular or substantially rectangular, and with a longitudinal vertical cross section (along the section plane IIA-IIA) with a shape that is an isosceles trapezoid or substantially an isosceles trapezoid with walls 15 symmetrical with respect to the longitudinal plane P, with the periphery uniformly toothed on the outside (teeth 16).

The teeth 16 (for example seven in number) are formed by longitudinal ridges of triangular shape, of which the vertices are directed upward or are horizontal, with an acute angle (imbricated). The lower teeth or the lower tooth of the component and the one or more upper teeth of the opening of the body form a means of pre-connection to each other by a snap-fit action.

The component 12 moreover has two end parts 17 of semicylindrical or substantially semicylindrical shape having walls of oval cross section which are symmetrical with respect to the section plane IIA-IIA 18, the oval configuration of which is directed outward and, as will be seen, is designed to cooperate with opposite walls of the opening 11.

Figure 2B:
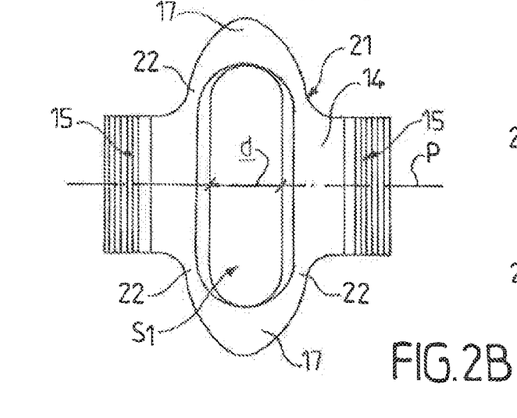

As is shown in FIGS. 2 and 2B, the walls 15 and 17 of the component 12 are solid and have no discontinuity.

The trapezoidal cross section has an angle at the base b (with respect to the small base of the trapezoid).

The angle between the walls 15 (corresponding to 2b−180°) is preferably between 10 and 30°.

More precisely, with reference to FIGS. 2B and 2C, the bore 13 has a horizontal cross section of oblong shape, like a cat's tongue, which will deform between a sectional shape S1 (FIG. 2B) and a sectional shape S2 narrowed at the middle (FIG. 2C).

The bore 13 comprises two opposite plane main walls 19, each comprising, on their inner face, a transverse rib 20, the transverse ribs 20 being mutually offset in height and having a square or rectangular cross section terminating in a fine bevel at the ends thereof, which will permit better blocking of the ends 2', 2" after insertion, the distance d between the two end edges 19 of the members before compression permitting free passage of the ends of the band 2.

The dimensions of the bore 13 are generally adapted to those of the band. In particular, the distance d and the length of the bore along the section plane P are chosen such that the two ends of the band are placed flat on each other. Indeed, any offset between the ends of the band is detrimental to correct clamping of the band in the device 1.

In practice, the distance d is slightly greater than twice the thickness of the band, and the length of the bore is slightly greater than the width of the band.

In the embodiment more particularly described here, the component 12 thus has a core 21 that is hollowed out by the bore 13 formed by the first central part 14 and the end parts 17. It has the opposite main walls 15, of which the outer face is inclined and forms the wedge connected by the two rounded end walls 17 which are designed to cooperate with the opening by friction, which will be described below.

The thickness e of the junctions 22 between main walls and end walls 17 is smaller (for example twice as thin) in order to permit the deformation by squeezing in the transverse direction (arrow 23) without deformation in the longitudinal direction (arrow 24) during the insertion of the component into the opening (cf. FIG. 2C).

Figure 3:
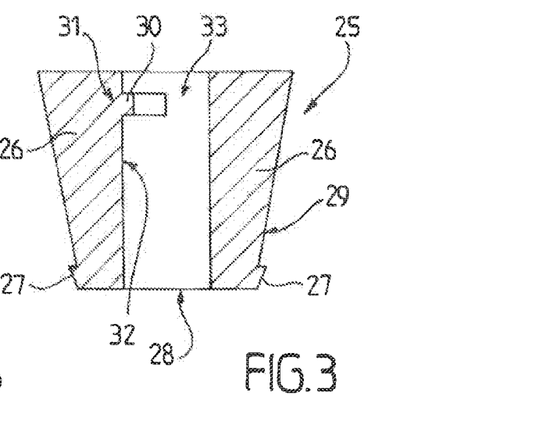
FIG. 3 is a longitudinal axial cross-sectional view of a component according to another embodiment of the disclosure.

FIG. 3 shows, in cross section, another embodiment of a component 25, of which the main walls 26 have only one tooth 27 at the bottom end 28 (small base of the trapezoid) on their outer face 29 and a single rib 30, in the upper part 31 (⁹⁄₁₀ of the height for example) on their inner face 32 of the bore 33.

Figures 4, 4A:
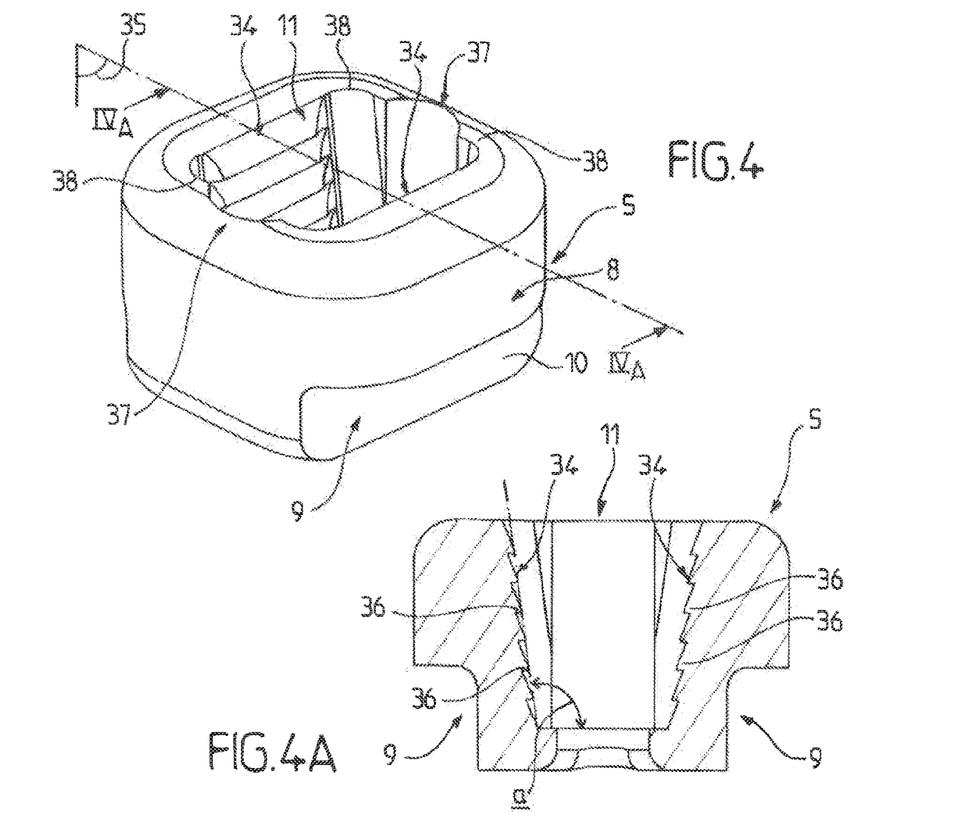
FIG. 4 is a perspective view of the base body from FIG. 1.
FIG. 4A is a cross-sectional view along IVA-IVA from FIG. 4.
Figure 4B:
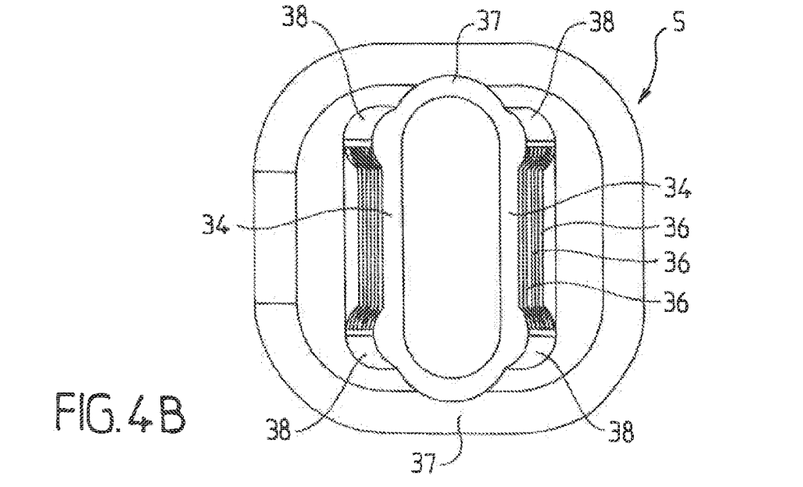
FIG. 4B is a plan view of the body from FIG. 4.

FIGS. 4, 4A and 4B show the base body 5 used with the component 12.

It is substantially parallelepipedal and has the through-opening 11.

The latter has two inner main longitudinal portions 34 which are symmetrical with respect to the axial plane perpendicular to the plane 35 (axial plane of the section IVA-IVA), having a trapezoidal longitudinal cross section with an angle to the base a, with teeth 36 or recesses of shapes complementing those of the outer faces of the walls 15 of the component, of identical or similar number (cf. FIG. 4A).

The disclosure is not limited to this embodiment and covers all means of complementary shapes provided on the inner face of the opening 11 and on the outer face of the component 12 for ensuring the pre-connection of the component and of the body or else a blocking of the component in the body.

The opening moreover has two end walls 37 which are designed to cooperate at least partially with the outer face of the walls 17 of the component by being of complementary shape, that is to say, in the embodiment more particularly described, with a half circular or half oval inner cross section.

Still in this described embodiment, the end walls are joined to the main walls by intermediate walls 38 which are of a curved shape and make up for the thicknesses of walls, which will leave recesses 39 (see FIG. 1B) after insertion.

Figure 5:
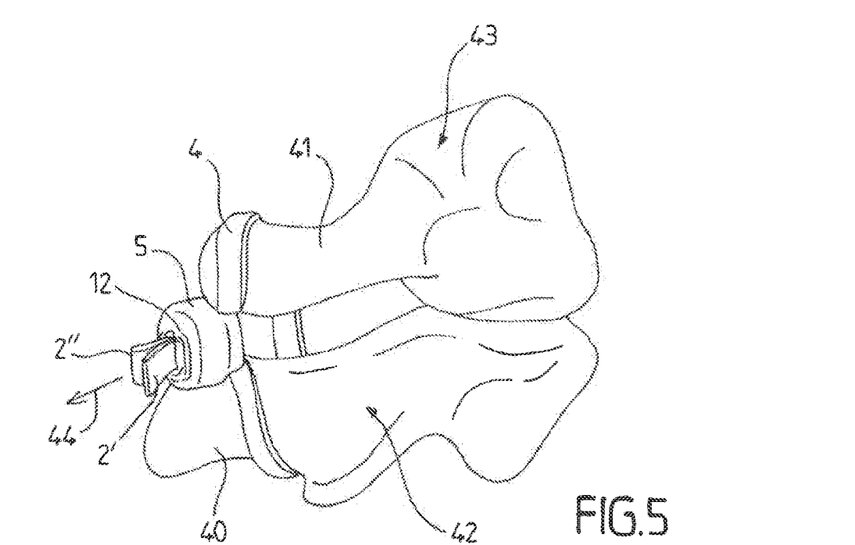
FIG. 5 shows schematically, and in profile, a device according to FIG. 1 in place on two adjacent vertebrae.

We will now describe, more particularly with reference to FIGS. 1A, 1B and FIG. 5, how bone parts 40 and 41 of two vertebrae 42, 43 are fixed to each other by the device according to the embodiment more particularly described.

Having passed the band in a loop formation around the two bone parts 40 and 41, the surgeon introduces the end portions 2 and 2' into the opening 11 of the body, then into the bore 13, and/or simultaneously into both if they are already pre-connected (summarily) to each other.

The body and the component are then moved toward the two bone parts using a known type of clamping tool, in the direction of arrow 44. The friction between the ends is sufficient to pre-position the device with the loop and at the desired distance.

Once the desired position has been obtained by the operator, the latter then inserts the component with force into the body in such a way as to bring the upper face 45 of the component flush with that 46 of the body, by pressing on the recesses 10.

This insertion by force causes the plastic or permanent deformation of the component.

The teeth of the component and of the body are then in engagement with each other and form a blocking system or non-return system that opposes their disassembly.

It has been found that a component made of polymer material does not damage the band and that a body made of titanium increases the efficiency of the clamping action.

The excess end parts are then cut off and the patient's back is closed.

Figure 6:
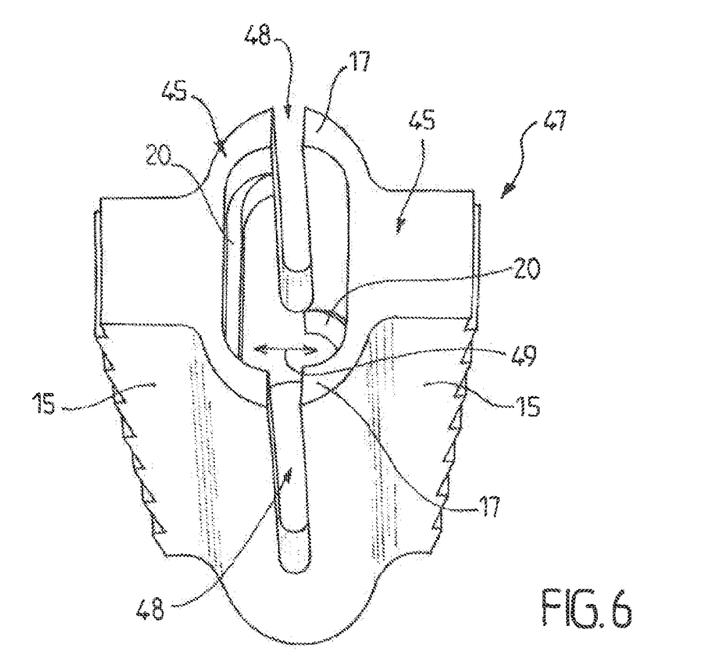
FIG. 6 is a schematic and perspective top view showing a component with a slit according to another embodiment of the disclosure.

FIG. 6 shows another embodiment of a component 47 according to the disclosure, of which the two end walls 17 moreover each comprise a slit 48 along a height hi less than the height H of the component, for example between 0.5 and 0.8 H. Each slit 48 extends through the corresponding wall 17 and opens out on the upper face 45 of the component 47, which will permit tightening of the component (arrow 49) when it is wedged in the opening of the body. The two slits 48 make it possible to guide the deformation of the component 47 and to avoid the risks of torsion or twisting of the component when it is inserted into the body.

Thus, the component has solid or continuous walls or else at most two walls having a slit, these two walls being opposite each other.

As will be appreciated, and as is also apparent from the above, the present disclosure is not limited to the embodiments more particularly described. Instead, it includes all variants thereof, in particular those in which all the elements are made of titanium or, by contrast, of a biocompatible plastic.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The embodiments of the invention in which an exclusive property or privilege is claimed are defined as follows:

1. A method for attaching a flat and flexible band on at least one bone part, with said band provided with two end portions, a rigid base body with a through-opening, and a retaining component that is insertable into said opening, with the retaining component being in the shape of a squeezable wedge comprising a central bore for passage of said opposite end portions of the flexible band, said method comprising:
   preconnecting partially beforehand said retaining component with said opening, wherein said retaining component having an outer peripheral face and said opening having an inner face, said preconnecting is made by snap fit action of said inner face with said peripheral face;
   introducing an end portion of the band into the opening and into the bore;
   passing the band around the bone part;
   passing the other end portion through the opening and the bore, thus forming a loop for gripping said bone part;
   tightening the loop to a desired size by pulling on the two end portions; and
   inserting said component with force into the opening, while deforming the bore in order to obtain a position in which said end portions are blocked by compression in the bore, the component then being deformed plastically.

2. The method according to claim 1, wherein the opening and the retaining component extending along a longitudinal axis and having shapes that are designed to cooperate by friction on at least one of their opposite parts in the direction perpendicular to said longitudinal axis, comprising the step of blocking the retaining component in the opening by said friction while inserting said component into said opening.

3. The method according to claim 1, wherein the component having a core hollowed out by the bore, of general oblong shape, comprising two opposite inclined main walls forming the wedge and two end walls extending about an axis, of which the faces are arranged to cooperate longitudinally with a corresponding recessed part of the opening, the thickness of the junctions between main walls and end walls being reduced, said deforming is obtained by squeezing in the transverse direction without deformation in the longitudinal direction during insertion of the component into the opening.

4. The method according to claim 1, for joining at least two adjacent vertebrae, wherein said end portion of the band being passed through the base body and the component, the flat band is placed around the two vertebrae to form said loop around said vertebrae, said other end portion is then passed through the opening and the bore, the vertebrae are brought closer by pulling on said ends, and the attachment is blocked by inserting the component with force into the body in the desired position, before cutting off the excess end portions of the band.

5. A method for attaching a flat and flexible band on at least one bone part, said band provided with two end portions, a rigid base body with a through-opening, and a retaining component that is insertable into said opening, wherein the retaining component being in the shape of a squeezable wedge comprising a central bore for passage of said opposite end portions of the flexible band, said central bore being of general oblong shape, comprising two opposite inclined main walls forming the wedge and two end walls extending about an axis, of which the faces are arranged to cooperate longitudinally with a corresponding recessed part of said opening, the thickness of the junctions between main walls and end walls being reduced, the method comprising:
   introducing an end portion of the band into the opening and into the bore;
   passing the band around the bone part, and passing the other end portion in the opening and the bore, thus forming a loop for gripping said bone part;
   tightening the loop to the desired size by pulling on the two end portions;
   finishing insertion of said retaining component with force into the opening; and
   deforming the bore in order to obtain a position in which said end portions are blocked by compression in the bore, said deforming being obtained by squeezing in the transverse direction without deformation in the longitudinal direction during insertion of the retaining component into the opening, said retaining component being thus deformed plastically.

6. The method according to claim 5, for attaching two bone parts together, further comprising, after said steps of introducing the end portions into the opening and into the bore, and tightening the loop to the desired size, moving the body and the component towards the two bone parts using a clamping tool into the direction of the bone parts, once the desired position has been obtained, inserting said retaining component with force into the opening.

7. The method according to claim 6, for attaching said two bone parts of the vertebra of a patient, wherein after opening the back of the patient, providing said steps of introducing, moving and pushing the body and the element each having upper faces, with, a clamping tool in the desired position, and then inserting said retaining component in such a way as to bring the upper face of the component flush with the upper face of the body, cutting of the excess end parts of the end portions, and then closing the patient's back.

8. The method according to claim 5, further comprising the initial step of preconnecting partially beforehand said retaining component with said opening, wherein said retaining component having on outer peripheral face and said opening having an inner face, said preconnecting is made by snap fit action of said inner face with said peripheral face.

\* \* \* \* \*